United States Patent
Dohi et al.

(10) Patent No.: US 9,708,558 B2
(45) Date of Patent: *Jul. 18, 2017

(54) METHOD FOR PREPARING COAL FOR COKE MAKING

(71) Applicant: JFE STEEL CORPORATION, Tokyo (JP)

(72) Inventors: Yusuke Dohi, Fukuyama (JP); Izumi Shimoyama, Kurashiki (JP); Kiyoshi Fukada, Fukuyama (JP); Hiroyuki Sumi, Kawasaki (JP)

(73) Assignee: JFE STEEL CORPORATION, Tokyo (JP)

(*) Notice: Subject to any disclaimer, the term of this patent is extended or adjusted under 35 U.S.C. 154(b) by 330 days.

This patent is subject to a terminal disclaimer.

(21) Appl. No.: 14/375,271

(22) PCT Filed: Feb. 25, 2013

(86) PCT No.: PCT/JP2013/001037
§ 371 (c)(1),
(2) Date: Jul. 29, 2014

(87) PCT Pub. No.: WO2013/128866
PCT Pub. Date: Sep. 6, 2013

(65) Prior Publication Data
US 2015/0007493 A1    Jan. 8, 2015

(30) Foreign Application Priority Data

Feb. 29, 2012 (JP) ................. 2012-043538

(51) Int. Cl.
*C10L 5/04* (2006.01)
*C10B 57/00* (2006.01)
(Continued)

(52) U.S. Cl.
CPC ............ *C10L 5/08* (2013.01); *C10B 57/04* (2013.01); *C10L 5/04* (2013.01); *C10L 9/10* (2013.01); *G01N 11/04* (2013.01)

(58) Field of Classification Search
CPC ...... C10L 5/00; C10L 5/04; C10L 5/28; C10L 5/32
See application file for complete search history.

(56) References Cited

U.S. PATENT DOCUMENTS

| 7,846,301 B2 * | 12/2010 | Katou | C10B 53/08 201/24 |
| 2013/0255142 A1 * | 10/2013 | Dohi | C10B 57/06 44/550 |
| 2014/0144071 A1 * | 5/2014 | Dohi | C10B 45/00 44/607 |

FOREIGN PATENT DOCUMENTS

| EP | 2612894 A1 | 7/2013 |
| EP | 2613137 A1 | 7/2013 |

(Continued)

OTHER PUBLICATIONS

Miyazu et al., "The Blending Design Using Many Kinds of Coal and the Evaluation System for Single Coal," *Nippon Kokan Technical Report*, 1975, vol. 67, pp. 125-137 (with Abstract).

(Continued)

*Primary Examiner* — Ellen McAvoy
*Assistant Examiner* — Ming Cheung Po
(74) *Attorney, Agent, or Firm* — Oliff PLC

(57) ABSTRACT

Method for preparing coal for coke making includes controlling particles size of coal or caking additive before arriving at the plant so particles content having diameter of 6 mm or more in the coal or caking additive reaches 30% by mass or less when the coal or caking additive has permeation distance of 15 mm or more. In another method, the relationship between a critical permeation distance and Gieseler (Continued)

maximum fluidity is obtained using permeation distances and Gieseler maximum fluidity values of one or more brands of coal or caking additive, particles size of coal or caking additive is controlled before arriving at the plant so particles content having diameter of 6 mm or more in coal or caking additive reaches 30% by mass or less when permeation distance of coal or caking additive is larger or equal to a critical permeation distance calculated from the Gieseler maximum fluidity.

16 Claims, 6 Drawing Sheets

(51) Int. Cl.
*C10L 5/08* (2006.01)
*C10B 57/04* (2006.01)
*C10L 9/10* (2006.01)
*G01N 11/04* (2006.01)

(56) References Cited

FOREIGN PATENT DOCUMENTS

| JP | A-55-3458 | 1/1980 |
| JP | A-2008-133383 | 6/2008 |
| JP | A-2010-190761 | 9/2010 |

OTHER PUBLICATIONS

International Search Report issued in International Patent Application No. PCT/JP2013/001037 dated May 28, 2013.

Dec. 7, 2015 European Search Report issued in European Application No. 15182966.0.

Feb. 11, 2015 Extended Search Report issued in European Application No. 13754918.4.

* cited by examiner (a)  (b)

(a)  (b)

(a)  (b)

METHOD FOR PREPARING COAL FOR COKE MAKING

TECHNICAL FIELD

The present invention relates to a method for preparing coal for coke making, in which coal for coke making is prepared using a testing method by which the thermo-plasticity of coal during carbonization can be evaluated with high accuracy and thereby the strength of coke can be increased.

DESCRIPTION OF RELATED ARTS

Coke used in a blast-furnace method, which is most commonly employed as an iron making method, plays several roles such as a reducing agent for iron ore, a heat source, and a spacer. It is important for stable, efficient operation of a blast furnace to maintain, the gas permeability of the blast furnace. Accordingly, production of coke having a high strength has been anticipated. Coke is produced by carbonization of a coal blend in a coke oven, the coal blend being prepared by mixing various coals for coke making that have been crushed in order to control their particle sixes. In carbonization, coal for coke making softens in the temperature range of about 350° C. to about 550° C. while foaming and swelling due to generation of volatile matter, which causes each particle of the coal to adhere to one another. Thus, a massive semicoke is formed. The send coke contracts in the subsequent process in which the temperature is increased to around 1000° C. and thereby hardens to form high strength coke. Therefore, the adhesiveness of coal during softening greatly affects the properties of coke made by carbonization, such as the strength and size of the coke.

In order to strengthen the adhesion of coal (coal blend) for coke making, a coke making method by adding a caking additive to a coal blend, the caking additive having high fluidity in a temperature range in which coal sol tens, has been commonly employed. Specific examples of the caking additive include tar pitch, petroleum pitch, solvent refined coal, and solvent extracted coal. Similarly to coal, the adhesiveness of the caking additive during softening greatly affects the properties of coke made by carbonization.

Therefore, hitherto, great importance has been placed on the evaluation of the thermo-plasticity of coal. The thermo-plasticity of coal has been measured by various methods and used as an index for managing coke strength. Coke strength, which is an important quality of coke, is greatly affected by the properties of coal, which is a raw material of coke. In particular, the degree of coalification and the thermo-plasticity of coal greatly affects coke strength. Thermo-plasticity is a property where coal softens when being heated and is generally measured and evaluated in terms of the fluidity, viscosity, adhesive property, or the like of plastic coal.

Among these properties for evaluating the thermo-plasticity of coal, the fluidity of coal during softening is generally measured by, for example, a method of coal fluidity measurement using a Gieseler plastometer method defined in JIS M 8801. A Gieseler plastometer method is a method in which coal that has been crushed to a size of 425 μm or less is charged in a predetermined crucible, heating is performed at a predetermined rate of temperature rise, the rotation speed of a stirrer under a predetermined torque is measured, and the thermo-plasticity of the sample is represented by dial division per minute.

Other known methods for evaluating thermo-plasticity are a method of measuring torque by a constant-rotation method, a method of measuring viscosity using a dynamic viscoelastometer, and a dilatometer method defined in JIS M 8801.

On the other hand, there has been, proposed a method for evaluating thermo-plasticity under conditions that are set with consideration of the conditions of plastic coal, placed in a coke oven (Patent Literature 1). In the method described in Patent Literature 1, measurement is made under conditions where plastic coal is constrained and the migration and permeation of the plastic coal into the peripheral void structures are simulated. A permeation distance measured by this method is an index of the thermo-plasticity of coal which is different from the indices employed in the methods of the related art.

CITATION LIST

Patent Literature

PTL 1: Japanese Unexamined Patent Application Publication No. 2010-190761

Non Patent Literature

NPL 1: Miyazu, et al.: "Nippon Kokan Technical Report", vol. 67, 1975, pp. 125-137

SUMMARY OF THE INVENTION

Technical Problem

However, in the method described in Patent Literature 1, it has not been clarified what preparation is to be performed on coal having a particular permeation distance in order to make coke having a high strength.

It is an object of the present invention to solve the above-described problems of the related art and to provide a method for preparing an individual brand of coal in which an appropriate preparation is performed on coal in accordance with the permeation distance of the coal, in order to increase coke strength or to suppress a reduction in coke strength.

Means for Solving the Problems

The features of the present invention for solving the above-described problems are as follows.

[1] A method for preparing coal for coke making, in which an individual brand of coal or caking additive is prepared at a time prior to arrival at a coke plant, the individual brand of coal or caking additive being used alone or in mixture with another coal as a raw material, for coke making.

When the individual brand of coal or caking additive has a permeation distance of 15 mm or more, a size of particles of the individual brand of coal or caking additive is controlled at the time prior to arrival at the coke plant so that a content of particles having a diameter of 6 mm or more in the individual brand of coal or caking additive reaches 30% by mass or less. The permeation distance is measured by a method including the following steps (A) to (D):

(A) crushing the individual brand of coal or caking additive until a content of particles having a diameter of 2 mm or less reaches 100% by mass and then packing a vessel with the individual, brand of coal or caking additive that has been crushed at a bulk density of 0.8 g/cm$^3$ and at a thickness of 10 mm to prepare a sample;

(B) arranging glass beads having a diameter of 2 mm on the sample at a thickness larger than or equal to the permeation distance;

(C) while applying a load of 50 kPa to an upper portion of the glass beads, performing heating in an inert gas atmosphere from room, temperature to 550° C. at a heating rate of 3° C./min; and (D) measuring a permeation distance of the softened sample that has permeated a layer composed of the glass beads.

[2] A method for preparing coal for coke making, in which an individual brand of coal or caking additive is prepared at a time prior to arrival at a coke plant, the individual brand of coal or caking additive being used alone or in mixture with another coal as a raw material for coke making.

When the individual brand of coal or caking additive has a permeation distance of 15 mm or more, a size of particles of the individual brand of coal or caking additive is control led at the time prior to arrival at the coke plant, so that a content of particles having a diameter of mm or more in the individual brand of coal or caking additive which is determined from a Hardgrove grindability index HGI of the individual brand of coal or caking additive using Expression (1) below is achieved:

Content (mass %) of particles having a diameter of 6 mm or more≤30+0.5×(HGI−60)    (1).

The permeation distance is measured by a method including the following steps (A) to (D);

(A) crushing the individual brand of coal or caking additive until a content of particles having a diameter of 2 mm or less reaches 100% by mass and then packing a vessel with the individual brand of coal or caking additive that has been crushed at a bulk density of 0.8 g/cm$^3$ and at a thickness of 10 mm to prepare a sample;

(B) arranging glass beads having a diameter of 2 mm on the sample at a thickness larger than or equal to the permeation distance;

(C) while applying a load of 50 kPa to an upper portion of the glass beads, performing heating in an inert gas atmosphere from room temperature to 550° C. at a heating rate of 3° C./min; and (D) measuring a permeation distance of the softened sample that has permeated a layer composed of the glass beads.

[3] A method for preparing coal for coke making, in which an individual brand of coal or caking additive is prepared at a time prior to arrival at a coke plant, the individual brand of coal or caking additive being used alone or in mixture with another coal as a raw material for coke making.

On the basis of a relationship between a critical permeation distance and a Gieseler maximum fluidity which is obtained from permeation distances and values of Gieseler maximum fluidity of one or more brands of coal or caking additive, when a permeation distance of the individual brand of coal or caking additive is larger than or equal to a critical permeation distance calculated from a Gieseler maximum fluidity of the individual brand of coal or caking additive on the basis of the relationship between the critical permeation distance and the Gieseler maximum fluidity, a size of particles of the individual brand of coal or caking additive is controlled at the time prior to arrival at the coke plant so that a content of particles having a diameter of 6 mm or more in the individual brand of coal or caking additive reaches 30% by mass or less.

[4] A method for preparing coal for coke making, in which an individual brand of coal or caking additive is prepared at a time prior to arrival at a coke plant, the individual brand of coal or caking additive being used alone or in mixture with another coal as a raw material for coke making.

On the basis of a relationship between a critical permeation distance and a Gieseler maximum fluidity which is obtained from permeation distances and values of Gieseler maximum fluidity of one or more brands of coal or caking additive, when a permeation, distance of the individual brand of coal or caking additive is larger than or equal to a critical permeation distance calculated from a Gieseler maximum fluidity of the individual brand of coal or caking additive on the basis of the relationship between the critical permeation distance and the Gieseler maximum fluidity, a size of particles of the individual brand of coal or caking additive is controlled at the time prior to arrival at the coke plant, so that a content of particles having a diameter of 6 mm or more in the individual brand of coal or caking additive which is determined from a Hardgrove grindability index HGI of the individual brand of coal or caking additive using Expression (1) below is achieved;

Content (mass %) of particles having a diameter of 6 mm or more≤30+0.5×(HGI−60)    (1).

[5] The method for preparing coal for coke making described in [3] or [4], in which the critical permeation distance is calculated using Expression (2) below:

Critical permeation distance=1.3×$a$×log MF$c$    (2)

where a represents a constant 0.7 to 1.0 times a coefficient of log MF in a regression line crossing an origin point which is obtained using permeation distances and values of log MF of one or more coals that fall within a range of common logarithm of Gieseler maximum fluidity log MF<2.5, and MFc represents a Gieseler maximum fluidity (ddpm) of the coal or caking additive to be prepared.

[6] The method for preparing coal for coke making described in [5], in which a represents a constant 0.7 to 1.0 times a coefficient of log MF in a regression line crossing an origin point which is obtained using permeation distances and values of common logarithm of Gieseler maximum fluidity log MF of one or more coals that fall within a range of 1.75<log MF<2.50.

[7] The method for preparing coal for coke making described in [3] or [4], in which the critical permeation distance is calculated using Expression (3) below:

Permeation distance=$a'$×log MF$c$+$b$    (3)

where a' represents a constant 0.7 to 1.0 times a coefficient of log MF in a regression line crossing an origin point which is obtained using permeation distances and values of log MF of one or more coals that fall within a range of common logarithm of Gieseler maximum fluidity log MF<2.5, b represents a constant that is larger than or equal to and five times or less an average of standard deviations each obtained by measuring, a plurality of times, the corresponding one of samples taken from, one or more brands used for preparing the regression line, and MFc represents a Gieseler maximum fluidity (ddpm) of the coal or caking additive to be prepared.

[8] The method for preparing coal for coke making described in [7], in which a' represents a constant 0.7 to 1.0 times a coefficient of log MF in a regression line crossing an origin point which is obtained using permeation distances and values of common logarithm of Gieseler maximum fluidity log MF of one or more coals that fall within a range of 1.75<log MF<2.50.

[9] The method for preparing coal for coke making described in any one of [1] to [8], in which the time prior to arrival at a coke plant is a time prior to shipping from, a coal field or a caking-additive manufacturing field.

Advantageous Effects of Invention

According to the present invention, an individual brand of coal having an appropriate particle size can be prepared in accordance with the permeation distance of the coal before being charged into a coke oven. By using the coal as a raw material for coke making, production of metallurgical, coke having a high strength can be realized.

DESCRIPTION OF EMBODIMENTS

Figure 1:
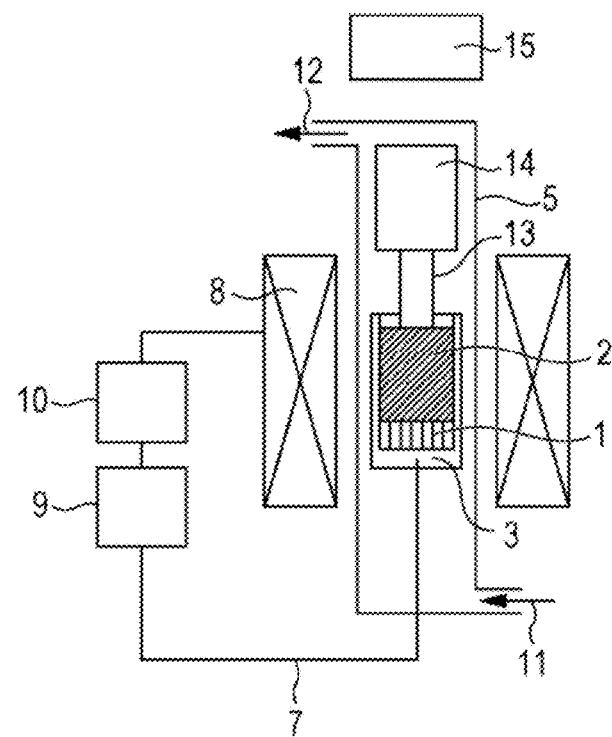
FIG. 1 is a schematic diagram illustrating an example of an apparatus used in the present invention for measuring the thermo-plasticity of coal or caking additive sample while applying a constant load, on the sample and a through-hole material having through holes from top to bottom surfaces.

Commonly, coke is produced by carbonization of a coal blend including a plurality of brands having various grades. In general, the grade of each brand is controlled at a coal field prior to shipping so as to satisfy the standard grade specified in a purchase contract or the like. Each brand of coal is crushed to some degree at a coal field area and then transported to a coke plant. The coal is further crushed and mixed with other brands at a coke plant. Thus, a coal blend for coke making is prepared.

During softening in a coke oven, coal is softened while being constrained by the adjacent layers. Since coal has low thermal conductivity, coal is not heated uniformly in a coke oven. Therefore, the state of coal changes from the oven-wall-side, which is a heating surface, in the following manner: a coke layer, a plastic layer, and a coal layer. During carbonization, a coke oven swells to some degree but negligibly deforms. Plastic coal is constrained by the adjacent coke layer and coal layer.

A number of void structures, such as voids between coal particles in a coal layer, voids between the particles of plastic coal, bulky pores formed due to volatilization of pyrolysis gas, and cracks formed in the adjacent coke layer, are present in the vicinity of the plastic coal. In particular, the cracks formed in a coke layer is considered to have a width of about several hundred micrometers to a few millimeters, which is larger than the voids between coal particles and the pores having a size of about several tens of micrometers to several hundred micrometers. Thus, it is considered that pyrolysis gas and liquid substances, which are by-products generated from coal, and plastic coal may permeate into such large voids formed in a coke layer. The shear velocity that acts on plastic coal during the permeation is supposed to vary by brand.

As described above, the conditions of constraint and permeation need to be set appropriately in order to measure the thermo-plasticity of coal under conditions simulating the circumstance of the periphery of plastic coal in a coke oven. The permeation distance used in the present invention is a method for evaluating the thermo-plasticity of coal or a caking additive under conditions sufficiently simulating the circumstance of the periphery of coal or a caking additive softened in a coke oven, which realizes the evaluation of the thermo-plasticity of coal with higher accuracy.

The inventors of the present invention have found that "permeation distance", which is a new index for evaluating thermo-plasticity, is an evaluation index superior to the indices employed in the related art in terms of controlling of coke strength. Specifically, the inventors have found that use of "permeation distance" realizes the evaluation of the coking properties of coal, which has not been able to be distinguished using the indices employed in the related art. Consequently, it became possible to distinguish coal that is suitably used for coke making and coal that is not suitably used for coke making. In addition, the inventors have found that, even when coal having an unfavorable permeation distance is used, the negative influence of the coal on coke properties can be eliminated by preparing the coal adequately. Thus, the present invention has been made. Permeation distance can be measured as follows.

Figure 8:
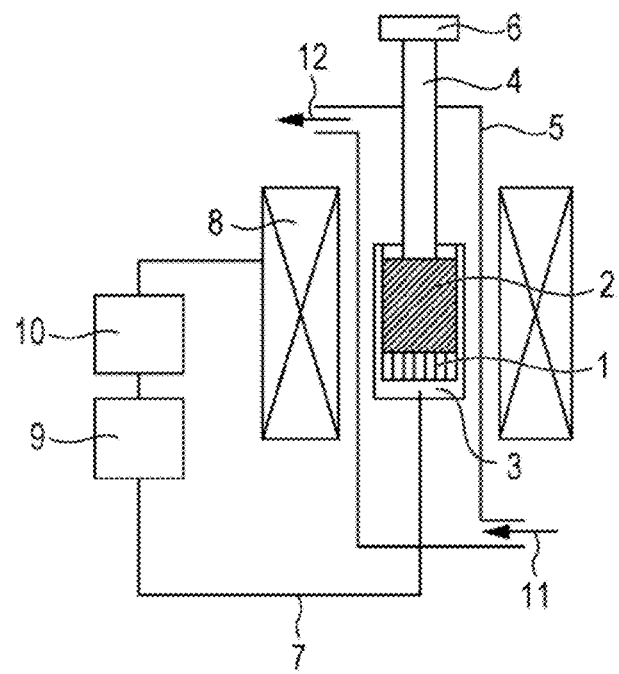
FIG. 8 is a schematic diagram illustrating an example of an apparatus used in the present invention for measuring the thermo-plasticity of a coal sample while keeping the volumes of the coal sample and a through-hole material constant.

FIG. 1 shows an example of an apparatus for measuring thermo-plasticity (permeation distance) used in the present invention. FIG. 1 shows an apparatus for heating a coal sample while applying a constant load to the coal sample and a through-hole material having through holes from top to bottom surfaces. A lower portion of a vessel 3 is packed with coal to form a sample 1. A through-hole material 2 is disposed on the sample 1. The sample 1 is heated to a temperature of the softening-beginning temperature or more to cause the sample to permeate through the through-hole material 2. Thus, the permeation distance is measured. Heating is performed in an inert gas atmosphere. The term "inert gas" herein refers to gas that does not react with coal in the range of temperature to be measured, and representative examples thereof include argon gas, helium gas, and nitrogen gas. Alternatively, in the measurement of the permeation distance, heating may be conducted so that the volume of the coal and the through-hole material is kept constant. FIG. 8 shows an example of an apparatus for measuring thermo-plasticity (permeation distance) which is used in this case.

When the sample 1 is heated while a constant load is applied to the sample 1 and the through-hole material 2 as shown in FIG. 1, the sample 1 undergoes swelling or contraction, which moves the through-hole material 2 in the vertical direction. Thus, the swelling coefficient of the sample during permeation of the sample can be measured on the basis of the displacement of the through-hole material 2. In order to measure the swelling coefficient, as shown in FIG. 1, an swelling coefficient detection rod 13 is disposed on the upper surface of the through-hole material 2, a weight 14 for applying a load is placed on the upper end of the swelling coefficient detection rod 13, and a displacement gage 15 is disposed on or above the weight 14. The displacement gage 15 may be a displacement gage capable of covering the range (−100% to 300%) of the swelling coefficient of the sample. Since the inside of the heating system needs to be maintained to be an inert gas atmosphere, a contactless displacement gage is suitably used. Desirably, an optical displacement gage is used. The inert gas atmosphere is preferably a nitrogen atmosphere. In the case where the through-hole material 2 is a layer packed with particles, a measure in which a plate is interposed between the through-hole material 2 and the swelling coefficient detection rod 13 is desirably taken because the swelling coefficient detection rod 13 may become disadvantageously buried in the particle-packed layer. The load is preferably applied equally over the upper surface of the through-hole material disposed on the upper surface of the sample. The pressure applied to the upper surface of the through-hole material is desirably 5 to 80 kPa, preferably 15 to 55 kPa, and most preferably 25 to 50 kPa. The pressure is preferably set in accordance with the swelling pressure of the plastic layer in a coke oven. However, the inventors have studied on the repeatability of measurement results and a capability of detecting a difference among various brands of coal and, as a result, have found that a pressure of about 25 to 50 kPa, which is slightly higher than the swelling pressure in the oven, is the most preferable as a measurement condition.

The heating means used is desirably a heating system capable of heating a sample at a predetermined rate of temperature rise while measuring the temperature of the sample. Specific examples of the heating means are an electric furnace, an external-heating system in which an electrically conductive vessel and high-frequency induction are used in combination, and an internal-heating system such as microwave. In the case where an internal-heating system is employed, an arrangement for making the temperature inside the sample uniform needs to be made. For example, a measure in which the thermal insulation properties of the vessel is enhanced may be preferably taken.

In order to simulate the behavior of coal or a caking additive during softening in a coke oven, the heating rate preferably agrees with the heating rate of coal in a coke oven. The heating rate of coal in a coke oven within the range of softening temperature is generally set to 2° C./min to 10° C./min, which varies depending on the position of the coal in the oven and operating conditions. The heating rate is desirably set to 2° C./min to 4° C./min and most desirably set to about 3° C./min on average. However, in the case where coal having low fluidity, such as non- or slightly caking coal, is used, the permeation distance and the amount of swelling of the coal measured at a heating rate of 3° C./min becomes small and may be difficult to be detected. It is commonly known that rapid heating of coal enhances the fluidity of the coal measured with a Gieseler plastometer. Therefore, for example, in the case where coal having a permeation distance of 1 mm or less is used, the heating rate may be increased to 10° C./min to 1000° C./min in order to enhance detection sensitivity.

For the purpose of evaluating the thermo-plasticity of coal or a caking additive, it is sufficient that a temperature range in which heating is performed is set so that heating is performed until the range of the softening temperature of coal or a caking additive is reached. With consideration of the range of the softening temperature of coal or a caking additive for coke making, it is sufficient that heating is performed within the range of 0° C. (room temperature) to 550° C., and, in particular, within the range of 300° C. to 550° C., which is the softening temperature of coal, at a predetermined heating rate.

Figure 2:
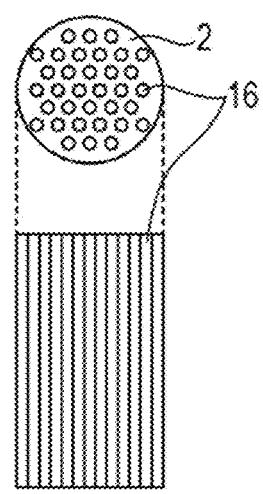
FIG. 2 is a schematic diagram illustrating an example of a through-hole material used in the present invention, which includes circular through-holes.
Figure 3:
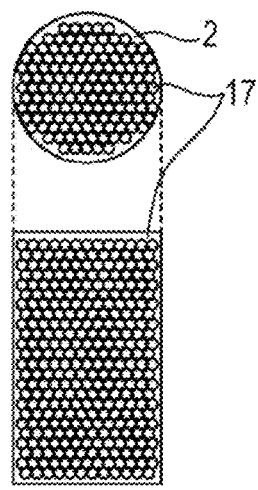
FIG. 3 is a schematic diagram illustrating an example of a through-hole material used in the present invention, which is a spherical-particle-packed layer.
Figure 4:
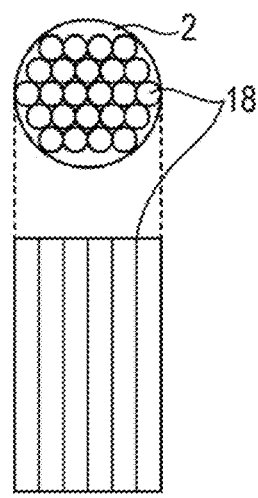
FIG. 4 is a schematic diagram illustrating an example of a through-hole material used in the present invention, which is a circular-cylinder-packed layer.

The through-hole material is desirably a material whose permeability coefficient can be measured or determined before being used. Examples of the form of the material include a one-piece material having through-holes and a particle-packed layer. Examples of the one-piece material having through-holes include a material having circular through-holes 16 as shown in FIG. 2, a material having rectangular through-holes, and a material having through-holes of different shapes. Examples of the particle-packed layer are roughly divided into spherical-particle-packed layers and non-spherical-particle-packed layers. An example of the spherical-particle-packed layers is a layer packed with packing particles 17, which are beads, as shown in FIG. 3. Examples of the non-spherical-particle-packed layers include a layer packed with particles of different shapes and a layer packed with circular packing cylinders 18 as shown in FIG. 4. It is desirable that the permeability coefficient of the through-hole material is uniform over the material in order to maintain the repeatability of measurement and is easily determined in order to simplify the measurement. Thus, as a through-hole material used in the present invention, in particular, a spherical-particle-packed layer is desirably used. The material of the through-hole material is not particularly limited as long as it negligibly deforms at a temperature in the range above the softening temperature of coal and, specifically, below 600° C., and does not react with coal. The height of the through-hole material is not particularly limited as long as the height is great enough for plastic coal to permeate therethrough and may be about 20 to 100 mm in order to heat a coal layer having a thickness of 5 to 20 mm.

It is necessary to estimate the permeability coefficient of large voids that are present in a coke layer in order to set the permeability coefficient of the through-hole material. The inventors of the present invention have studied on the permeability coefficient that is particularly desirable in the present invention, such as discussion of factors causing the large voids and estimation of the size of the large voids. As a result, the inventors have found that a permeability coefficient of $1\times10^8$ to $2\times10^9$ $m^{-2}$ is the optimal value. The permeability coefficient used herein is derived in accordance with Darcy's law represented by Expression (4) below:

$$\Delta P/L = K \cdot \mu \cdot u \quad (4)$$

where $\Delta P$ represents the pressure loss [Pa] in the through-hole material, L represents the height [m] of the through-hole material, K represents a permeability coefficient [$m^{-2}$], $\mu$ represents the viscosity [Pa·s] of a fluid, and u represents the velocity [m/s] of a fluid. For example, when the through-hole material used is a layer of glass beads having a uniform diameter, it is desirable to select glass beads having a diameter of about 0.2 to 3.5 mm in order to achieve the preferable permeability coefficient described above. More desirably, glass beads having a diameter of 2 mm is selected.

Coal or a caking additive used as a measurement sample is crushed and then packed at a predetermined thickness and at a predetermined bulk density. The size of the crushed particles may be set to the size of the particles of coal charged in a coke oven (the proportion of particles having a diameter of 3 mm or less is about 70% to 80% by mass). Crushing is preferably performed so that the proportion of particles having a diameter of 3 mm or less is 70% by mass or more. However, considering that the measurement is conducted using a small apparatus, it is particularly preferable to use coal or a caking additive that are crushed so that all the particles thereof have a diameter of 2 mm or less. The bulk density at which the crushed product is packed may be set 0.7 to 0.9 g/cm$^3$ in accordance with the bulk density of the coke oven. The inventors have studied on repeatability and detectability and found that the density is preferably set to 0.8 g/cm$^3$. The thickness of the packed layer may be set to 5 to 20 mm in accordance with the thickness of the plastic layer in the coke oven. The inventors have studied on repeatability and detectability and found that the thickness is preferably set to 10 mm.

The principal conditions of measurement of permeation distance are described below:

(A) crushing coal or a caking additive until the proportion of particles having a diameter of 2 mm or less reaches 100% by mass and then packing a vessel with the crushed coal or caking additive at a thickness of 10 mm and at a bulk density of 0.8 g/cm$^3$ to prepare a sample;

(B) arranging glass beads having a diameter of 2 mm on the sample at a thickness (normally, 80 mm) larger than or equal to the permeation distance;

(C) while applying a load on the upper portion of the glass beads at 50 kPa, performing heating from room temperature to 550° C. at a heating rate of 3° C./min in an inert gas atmosphere; and (D) measuring the permeation distance of the softened sample that permeated into a layer of glass beads.

Ideally, it is desirable to always, continuously measure the permeation distance of plastic coal or caking additive during heating. However, it is difficult to conduct the continuous measurement, for example, because of the influence of tar generated from the sample. The swelling and permeation of coal due to heating are irreversible phenomena: once swelling or permeation occurs, the shape of coal almost remains as it was even when being cooled. Thus, alternatively, the maximum permeation distance that occurred during heating may be measured by cooling the entire vessel after completion of permeation of the plastic coal and then measuring the permeation distance in the cooled vessel. For example, the through-hole material taken from the cooled vessel can be directly measured using a vernier caliper or a ruler. In the case where the through-hole material is constituted by particles, plastic coal that permeated through interparticle gaps causes the entirety of a portion of the particle layer through which the plastic coal permeated to be adhered. Thus, by determining the relationship between the mass and the height of the particle-packed layer in advance, the mass of the adhering particles can be derived by measuring, after completion of permeation, the mass of particles that are not adhering to one another and then subtracting the mass of the particles from the initial mass. The permeation distance can be calculated from the mass of the adhering particles.

The above-described superiority of permeation distance is theoretically assumed considering that the permeation distance is measured under conditions similar to the conditions of a coke oven. In addition, the results of studying the effect of permeation distance on coke strength have also clarified the superiority of permeation distance. Actually, by using the evaluation method according to the present invention, it was clarified that the permeation distance of coal varies by brand even among coals having substantially same log MF (the common logarithm of the maximum fluidity measured by a Gieseler plastometer method). Furthermore, it was confirmed that the influence of making coke by mixing coals having different permeation distances on the strength of the coke also varies.

In the thermo-plasticity evaluation performed in the related art, in which a Gieseler plastometer is used, it has been believed that, the higher the fluidity of coal, the stronger the effect of adhering the particles of the coal to one another. On the other hand, the study on the relationship between permeation distance and coke strength showed that mixing of coal having an excessively large permeation distance results in formation of oversized voids and formation of a structure constituted by thin pore-walls during coking, which reduces coke strength to a value lower than a value estimated from the average property of the coal blend. This is presumably because coal having an excessively large permeation distance permeates between the peripheral coal particles by a significant degree and a portion in which the coal particle was present remains as a large cavity, which results in formation of a void. It was found that, among coals that are found to have high fluidity by a thermo-plasticity evaluation using a Gieseler plastometer, in particular, the quantity of the created oversized voids that remain in each coke varies depending on the permeation distance of the coal. The above relationship was also observed among caking additives.

The inventors of the present invention have conducted extensive studies and, as a result, found that coal having a permeation distance of a particular critical permeation distance or more reduces coke strength when being mixed in a raw material for coke making and that it is effective to define the critical permeation distance in the following three methods (I) to (III).

(I) The critical permeation distance is defined by the following expression:

$$\text{Critical permeation distance} = 1.3 \times a \times \log MFc \quad (2)$$

Where a represents "a" constant 0.7 to 1.0 times the coefficient of log MF in a regression line crossing the origin point which is obtained using the measured permeation distances and values of log MF of one or more coals that fall within the range of log MF<2.5; and MFc represents the Gieseler maximum fluidity (ddpm) of the coal whose critical permeation distance is to be determined.

(II) The critical permeation distance is defined by the following expression:

$$\text{Critical permeation distance} = a' \times \log \text{MF}c + b \qquad (3)$$

Where "a'" represents a constant 0.7 to 1.0 times the coefficient of log MF in a regression line crossing the origin point which is obtained using the measured permeation distances and values of maximum fluidity of one or more coals that fall within the range of log MF<2.5; "b" represents a constant that is larger than or equal to and five times or less the average of standard deviations each obtained by measuring, a plurality of times, the corresponding one of samples taken from one or more brands used for preparing the regression line; and MFc represents the Gieseler maximum fluidity (ddpm) of the coal whose critical permeation distance is to be determined.

(III) The critical permeation distance is set to 15 mm, which is a permeation distance measured when a coal sample is heated to 550° C. at a heating rate of 3° C./min under a load of 50 kPa using glass beads having a diameter of 2 mm as a through-hole material, the coal sample being prepared so that the content of particles having a diameter of 2 mm or less is 100% by mass and being packed in a vessel at a bulk density of 0.8 g/cm$^3$ and at a thickness of 10 mm.

The three methods (I) to (III) for determining critical permeation distance are described above because permeation distance may vary depending on the measurement conditions, such as load, the rate of temperature rise, the type of through-hole material, and the structure of an apparatus; and because the inventors of the present invention have studied with consideration of the cases where the measurement conditions employed are different from the conditions employed in the examples described in the present invention and, as a result, have found that it is effective to employ the method for determining critical permeation distance such as the methods (I) to (III) above.

The constants "a" and "a'" in the expressions used in the methods (I) and (II) are determined to be 0.7 to 1.0 times the coefficient of log MF in a regression line crossing the origin point obtained using the measured permeation distances and values of maximum fluidity of one more coals that fall within the range of log MF<2.5. This is because, although there is a substantially positive correlation between the maximum fluidity and the permeation distance of coal within the range of log MF<2.5, a brand that causes a reduction in strength has a permeation distance that considerably deviates from the correlation in the positive direction. The inventors of the present invention have conducted extensive studies and, as a result, found that a brand that causes a reduction in strength is a brand having a permeation distance 1.3 times or more the permeation distance determined from the value of log MF of the coal using the above-described regression expression. Thus, the critical permeation distance is defined as described in (I). In the method (II), in order to detect a brand that deviates from the above-described regression expression by more than the measurement error in the positive direction, the inventors have found that a brand that reduces strength is a brand that has a permeation distance larger than or equal to a permeation distance obtained from the regression expression plus a value that is larger than or equal to and five times or less the average of the standard deviations each obtained by measuring the corresponding sample a plurality of times. Thus, the constant b of the critical permeation distance is defined as described in (II). Therefore, the constant b may be set to a value equal to or more and five times or less the standard deviations each obtained by measuring the corresponding sample a plurality of times. In the measurement conditions described in Examples of the present invention, the constant b was set to about 0.6 to 3.0 mm. Both the expressions define the range of the permeation distance that may cause a reduction in strength on the basis of the value of log MF of the coal. This is because, generally, the larger the MF value, the larger the permeation distance, and it is important to determine how much the permeation distance deviates from the correlation. The regression line may be obtained by linear regression based on a publicly known least-square method. The number of coals used for obtaining a regression line is preferably large because, the larger the number of the coals used, the smaller the regression error. In particular, a brand having a small. MF tends to have a small permeation distance, and the error tends to be large. Therefore, it is particularly preferable to obtain a regression line using one or more coals that fall within the range of 1.75<log MF<2.50.

The ranges of the constants "a", "a'", and b are defined above because employing the smallest values possible allows coal that causes a reduction in strength to be detected with more accuracy. The values of the constants "a", "a'", and "b" may be controlled in accordance with the operational demands. However, an excessively small constant "a", "a'", or b increases the number of coals that are supposed to produce a negative influence on coke strength and causes a problem of misidentifying coal that does not actually cause a reduction in strength as coal that causes a reduction in strength. Therefore, "a" and "a'" are set to a value 0.7 to 1.0 times the slope of the regression line, and "b" is set to a value equal to or more and five times or less the average of the standard deviations each obtained by measuring the corresponding sample a plurality of times. The constants "a", "a'", and "b" can be appropriately set within the above-described ranges. These constants may be set on the basis of the relationship between the permeation distance and the maximum fluidity of coal which is determined in advance as described above. When measurements are made by the method described in Example 1 below, "a" and "a'" are set to 1.89 to 2.70 and "b" is set to 0.6 to 3.0. The types of coal and blending proportion that are employed in Example 1 are the general conditions for coke making. The upper limits of the above-described ranges are preferably employed in order to prevent misidentifying coal that does not actually cause a reduction in strength as coal that causes a reduction in strength. Thus, when it is assumed that the permeation distance is measured by a method similar to the method employed in Example 1, Expressions (2') and (3') below may be employed instead of Expressions (2) and (3). In this case, the values of "a", "a'", and "b" are not necessarily calculated and set in advance. Expressions (2), (3), (2'), and (3') are not necessarily determined every time an individual brand of coal is prepared and may be determined at a field different from the field where the individual brand of coal is prepared.

$$\text{Critical permeation distance} = 1.3 \times 2.7 \times \log \text{MF}c \qquad (2')$$

$$\text{Critical permeation distance} = 2.7 \times \log \text{MF}c + 3.0 \qquad (3')$$

If coal having a permeation distance larger than or equal to the critical permeation distance calculated by any one of the above-described methods (I) to (III) is used as raw material coal for coke making (raw material coal) in a normal operation, oversized voids are formed during coking and a structure constituted by thin pore-walls is formed, which leads to a reduction in coke strength.

However, the inventors of the present invention have found that, even when a coal blend including coal having a permeation distance larger than or equal to the critical permeation distance is used as a raw material of coke, a reduction in strength can be suppressed by changing the size of the particles of the coal. The process of the consideration is described below with reference to schematic diagrams.

Figure 5:
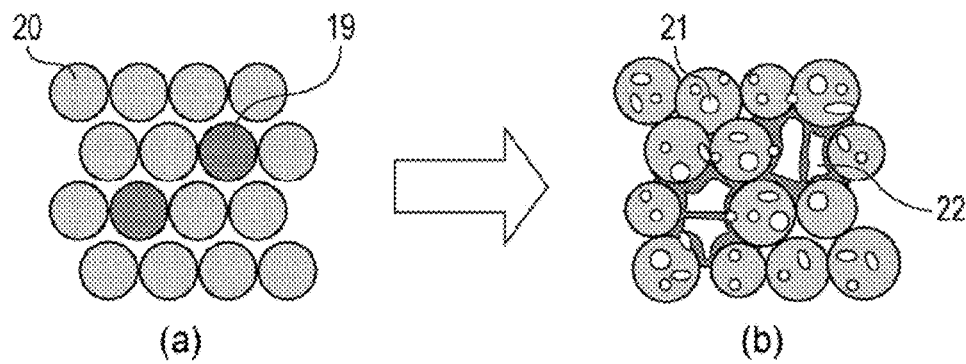
FIG. 5 includes schematic diagrams illustrating conditions where a void structure is formed during coking of a coal blend including coal having a permeation distance of the critical permeation distance or more; (a) illustrates a condition before coking where the coal is packed, and (b) illustrates a condition after coking where voids are formed.

FIG. 5 schematically illustrates a condition where a void structure is formed during coking of a coal blend including coal having a permeation distance larger than or equal to the critical permeation distance. During coking, the particles of coal 19 having a permeation distance larger than or equal to the critical permeation distance permeates into gaps between the packed particles and into oversized voids. Consequently, thin pore-walls are formed and oversized voids 22 are left at the portions where the particles were originally positioned, which leads to a reduction in coke strength (FIG. 5(b)).

Figure 6:
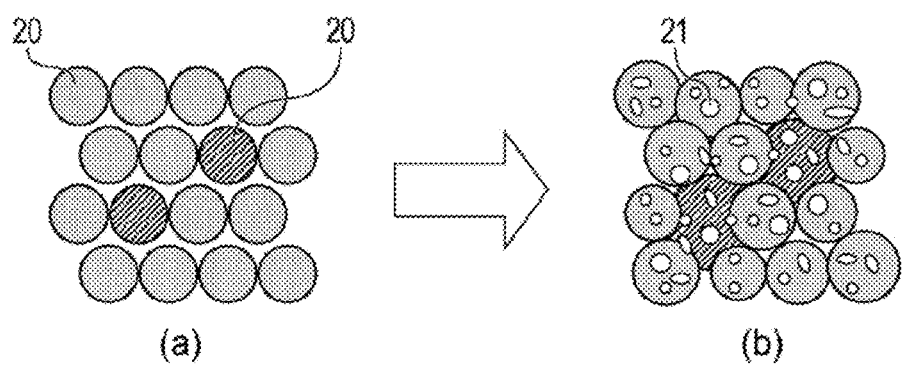
FIG. 6 includes schematic diagrams illustrating conditions where a void structure is formed during coking of a coal blend including coal having a permeation distance of less than the critical permeation distance; (a) illustrates a condition before coking where the coal is packed, and (b) illustrates a condition after coking where voids are formed.

FIG. 6 schematically illustrates a condition where a void structure is formed during coking of a coal blend including coal having a permeation distance less than the critical permeation distance. (During coking, the particles of coal 20 having a permeation distance less than the critical permeation distance negligibly permeates into voids between the packed particles and into oversized voids. Therefore, thin pore-walls are less likely to be formed and oversized voids 22 are less likely to be left at the portions where the particles were originally positioned. Thus, a reduction in coke strength is less likely to occur (FIG. 6(b)).

Figure 7:
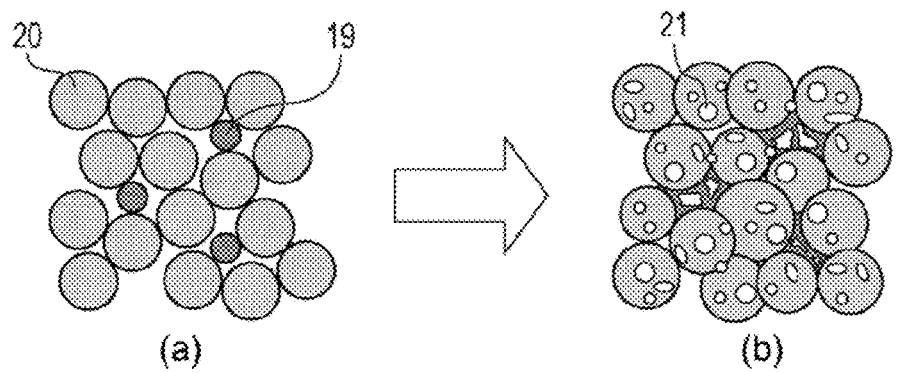
FIG. 7 includes schematic diagrams illustrating conditions where a void structure is formed during coking of a coal blend including coal having a permeation distance of the critical permeation distance or more, the coal having been crushed into fine particles prior to being mixed in the coal blend; (a) illustrates a condition before coking where the coal is packed, and (b) illustrates a condition after coking where voids are formed.

FIG. 7 schematically illustrates a condition where a void structure is formed during coking of a coal blend including coal 19 having a permeation distance larger than or equal to the critical permeation distance, the coal 19 having been crushed into fine particles prior to being mixed in the coal blend. In this case, during coking, the particles of coal 19 having a permeation distance larger than or equal to the critical permeation distance permeate into voids between the packed particles and into oversized voids to a large degree. However, the sizes of voids formed in the portions where the particles were originally positioned become small, which suppresses a reduction in coke strength (FIG. 7(b)).

As described in the above consideration, in the case where coal having a permeation distance larger than or equal to the critical permeation distance is mixed in a coal blend, a measure in which the size of the particles of the coal is reduced may be taken, which suppresses the formation of oversized voids and a reduction in the strength of coke made by carbonization.

A caking additive having a permeation distance larger than or equal to the critical permeation distance, which is mixed in a coal blend, may also cause a reduction in coke strength due to a mechanism similar to that described above. Therefore, the size of the particles of such a caking additive is preferably controlled prior to the arrival at a coke plant so as to reach a particle size similar to a particle size to which the size of the diameter of coal having a permeation distance larger than or equal to the critical permeation distance is to be controlled.

Figure 13:
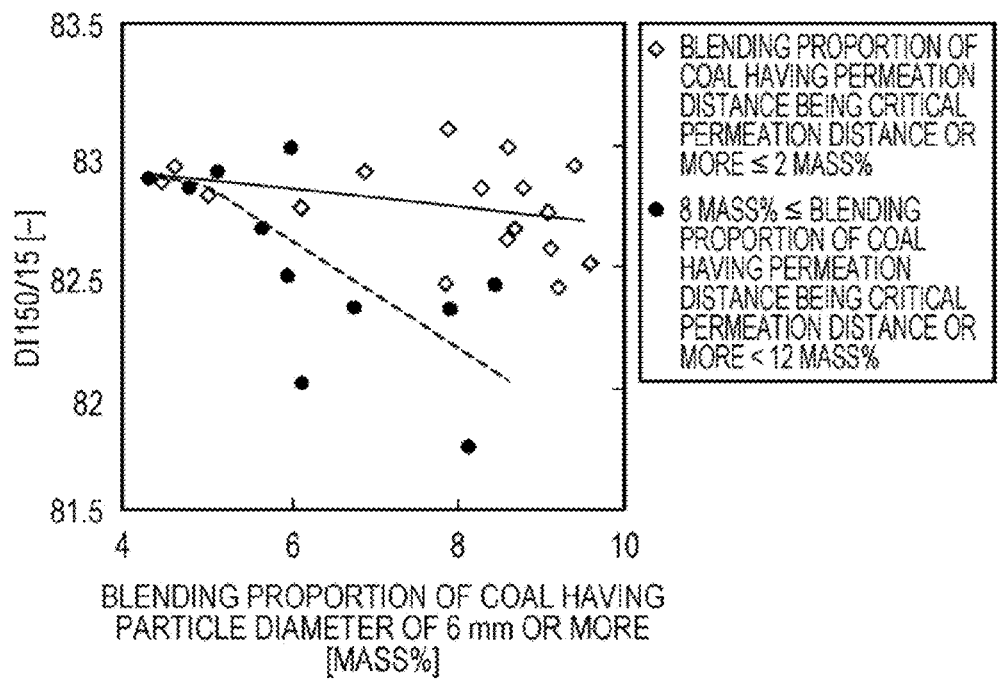
FIG. 13 is a graph showing the results of measuring the drum index of coke in Example 2.

The inventors of the present invention have further studied how small the size of the particles of the coal having a permeation diameter larger than or equal to the critical permeation distance is to be reduced before being mixed in a coal blend in order to suppress a reduction in strength. As a result, the inventors have found that a significant reduction in strength does not occur when the content of particles having a size of 6 mm or more in the coal is 5% by mass or less. In Example 2 below, as shown in FIG. 13, in the case where the content of particles having a size of 6 mm or more in coal was 5% by mass or less, although 8% by mass (and less than 12% by mass) of coal having a permeation distance larger than or equal to the critical permeation distance was mixed, DI150/15 was as large as that obtained in the case where a small amount of the coal, that is, 2% by mass or less, was mixed in a coal blend. Thus, the influence of mixing the coal having a permeation distance larger than or equal to the critical permeation distance, that is, a reduction in coke strength, was suppressed. However, in a coke plant, in which generally 10 to 15 brands of coal are mixed together in order to make coke, controlling the size of the particles of a particular brand of coal only to a particular particle size complicates the operation. Accordingly, the inventors have considered that, by controlling the size of the particles of coal having a permeation distance larger than or equal to the critical permeation distance prior to arrival at a coke-making plant, a reduction in coke strength can be suppressed without performing any special crushing in a coke plant.

The size of the particles of coal can be measured by, under a condition where coal is dried until the moisture content in the coal reaches 6% by mass or less, screening the coal through a sieve having predetermined mesh and calculating the ratio of the mass of the particles that have passed through or that remain on the sieve to the total mass of the sample. The moisture content in coal is preferably 6% by mass or less because formation of granulated particles among coal particles and adhesion of fine powder to coarse particles are less likely to occur and consequently an error in the measured particle size is less likely to occur.

The inventors have also found that, in the case where standard crushing conditions for a coke plant are employed, in order to prepare an individual brand of coal to be charged to a coke oven so that the content of particles having a diameter of 6 mm or more is 5% by mass or less, the content of particles having a diameter of 6 mm or more in the coal is controlled to be 30% by mass or less prior to arrival at a coke plant. In a coke plant, since generally 10 to 15 brands of coal are mixed together in order to make coke, crushing is performed after mixing the multiple brands of coal. In this case, if a particular brand of coal has a large particle size, it is difficult to strengthen crushing conditions of the post-blending crushing in order to reduce the particle size of the particular brand only. The inventors of the present invention have conducted further studies and found that, when the content of particles having a diameter of 6 mm or more in coal is controlled to be 30% by mass or less prior to arrival at a coke plant, the content of particles having a diameter of 6 mm or more in the individual brand of coal to be charged into a coke oven becomes 5% by mass. Thus, the present invention have been made.

Considering the hardness of coal, it is preferable that, the harder the coal, the smaller the size of the particles of the coal prior to arrival at a coke plant. Since HGI (Hardgrove grindability index) is generally employed as an index of the hardness of coal, a method of controlling the size of the particles of an individual brand of coal to be within the range specified by Expression (1) below is proposed.

$$\text{Content (mass \%) of particles having a diameter of 6 mm or more} \leq 30 + 0.5 \times (\text{HGI} - 60) \qquad (1)$$

The higher the HGI of coal, the softer the coal. Thus, under the same crushing conditions, the higher the HGI of coal, the smaller the size of the particles of the crushed coal. Therefore, when the crushing target in a coke plant is constant, a high-HGI coal can achieve a predetermined target particle size even when the size of the particles of the coal supplied is large (the content of particles having a diameter of 6 mm or more in the coal is large) when being supplied to a crusher in a coke plant. In crushing of coal in a coke plant, in many cases, coals that arrived at the coke plant are mixed together and the resulting coal blend is crushed. Thus, both a brand having a high HGI and a brand having a low HGI and both a brand having a large particle size and a brand having a small particle size are supplied to a crusher at the same time. In order to reduce the size of the particles of a particular brand only (e.g., a coal brand having a large permeation distance according to the present invention) by crushing, it is the easiest to reduce the size of the particles of the particular brand before the brand is supplied to the crusher. Thus, in the present invention, controlling of particle size is performed before coal arrives at a coke plant or when the coal is shipped from a production field. The inventors of the present invention have examined the grindability and HGI of coal having a large permeation distance, which produces a negative influence on coke strength when the size of the particles of the coal charged into a coke oven is large. As a result, the inventors have found that the HGI of a high-permeation-distance coal having a permeation distance of 15 mm or more as measured by the method described in Example 1 is about 60 to about 80; and that, in the case where coal having a HGI of about 60, which is the hardest high-permeation distance brand, is used, in order to control the content of particles having a size of 6 mm or more to be 5% by mass or less by crushing the high-permeation distance coal under crushing conditions such that the resulting coal blend has a particle size suitable for coke making (the content of particles having a size of 3 mm or less is 70% to 80% by mass), the proportion of particles having a size of 6 mm or more in particles supplied to a crusher is set to 30% by mass. The inventors have also found that, when HGI increases by 1 (become soft), the proportion of the particles having a size of 6 mm or more in particles supplied to a crusher in a coke plant can be increased by 0.5% by mass (become coarse particles) while maintaining the content of the particles having a size of 6 mm or more in the crushed particles to be 5% by mass; and that it is more preferable to control particle size of coal prior to arrival at a coke plant or when being shipped from the production field in accordance with the HGI of the brand. On the basis of the above-described findings, it is considered that the particle size of coal before being arrived at a coke plant or when being shipped from the production field is more preferably defined using Expression (1) below.

Content (mass %) of particles having a diameter of 6 mm or more$\leq 30+0.5\times(HGI-60)$ (1)

Controlling the size of the particles of a particular brand only which is supplied to a crusher is particularly effective when crushing is performed after blending of coal as described above. However, this method also has an advantage in that, even when blending is performed after each brand of coal is crushed to the size of particles to be charged into a coke oven, it is not necessary to control the crushing conditions (Crushing power, supplying rate, etc.) for a particular brand only and coal can be crushed to a desired size.

The HGI of coal ranges normally from 40 to 100, and the HGI of the high-permeation-distance coal ranges from about 60 to about 80 as described above. Thus, when the content of particles having a diameter of 6 mm or more is 30% by mass or less, the effect of the present invention can be produced. Considering the variation of HGI over coals, the content of particles having a diameter of 6 mm or more is more preferably 20% by mass or less.

It is more preferable that the size of the particles of coal having a large permeation distance is as small as possible. However, as described above, a severe reduction in coke strength resulting from mixing of coal having a large permeation distance can be prevented by controlling the size of the particles of coal so that the content of particles having a particle diameter of 6 mm or more is 5% by mass or less. In addition, generally, the size of the particles of coal to be charged into a coke oven is controlled so that the content of particles having a diameter of 6 mm or more is about 5% by mass or less by crushing or the like at a coke plant after the coal arrives at the coke plant. Therefore, the size of the particles of coal is not necessarily to be reduced so that the content of particles having a diameter of 6 mm or more reaches less than 5% by mass before the coal arrives at a coke plant.

Examples of a method for controlling the size of the particles of an individual brand include, when the size of particles of coal is reduced, a method of mining coal so that the size of the particles is reduced in a coal mining process; and controlling the size of the particles of coal by crushing, sizing, and screening in a coal-cleaning step or a coal-blending step performed between mining and shipping. In a coal mine, the grade of coal is determined for each coal bed in advance. Thus, measurement of permeation distance may be conducted at the same time, and controlling of particle size may be performed on the basis of the measured value by the above-described method or the like. A conventional impact crusher or hammer crusher may be used for crushing coal. These crushers are more preferably used in combination with a sieve because this allows only coarse-particle portions that causes a reduction in strength to be crushed, which realizes an efficient particle size control. The size of the particles of coal varies by lot because it inevitably changes depending on various conditions such as the place and the timing of mining, the apparatus used, transportation after mining, and storage. Accordingly, lots having different particle sizes may be mixed together to achieve a predetermined particle size.

The term "individual brand of raw material coal" is defined as a unit of raw material coal that is managed as a single lot when arriving at a coke making plant or when being shipped from a coal field. The expression "managed as a single lot" refers to, for example, the case where the properties of the entire lot is represented by a representative analysis value of a sampling from the lot, the case where the coal is stacked on a coal yard as a single lot, the case where the coal is charged in a single coal bin, or the case where the coal is traded as a single lot or as a single brand name in a purchase contract. Thus, the term "preparation of raw material coal" used herein is defined as an individual brand of raw material coal in the case where the coal is treated before the coal arrives at a coke making plant, except for the case where the treatment is performed after the coal arrives at a coke making plant.

The expression "arrival at a coke plant" refers to receiving coal at a coal yard or a coal hopper disposed in a coke plant in order to pulverize coal into a particle size suitable for coke making or to mix the coal with other brands of coal in a coke plant. For example, in ironworks located in a waterfront area, generally, coal is received in a raw-material quay and then transported to a coal yard disposed in a coke plant. In this case, the time when the coal arrives at the quay is considered to be arrival at a coke plant.

The term "shipping from a coal field" herein refers to sending the individual brand of coal from a mine or a shipping base by transportation means such as a ship, a freight car, a truck, or a conveyer. In the present invention, the shipping means (e.g., a ship or a freight car) and a process for shipping are not particularly limited (when coal is shipped by a freight car and then transshipped to a ship, both are referred to as "shipping") as long as the coal is shipped as an individual brand of coal from a mine, a shipping base, or the like. This is because, once coal is identified as an individual brand of coal, a change in the composition or the size of the particles of coal (except for inevitable changes) does not occur thereafter.

EXAMPLES

A method of determining the pretreatment conditions suitable for coal having a permeation distance larger than or equal to the critical permeation distance is described below.

Example 1

Confirmation of the Difference Between Permeation Distance and Thermo-Plasticity (Gieseler Maximum Fluidity) Used in the Related Art, Influence of a Difference in Permeation Distances on Coke Strength, and Determination of Critical Permeation Distance The permeation distances of 18 types of coal (Coal A to Coal R) and a caking additive (Caking additive S) were measured. Table 3 shows the properties of the coals and the caking additive used, where Ro represents the mean maximum reflectance of vitrinite of coal according to JIS M 8816, log MF represents the common logarithm of maximum fluidity (MF) measured by a Gieseler plastometer method, and volatile matter (VM) and ash content (Ash) are values measured by a proximate analysis according to JIS M 881.2.

The permeation distances were measured using the apparatus shown in FIG. 1. Since a high-frequency induction heating system was employed as a heating system, in FIG. 1, the heating element 8 was an induction heating coil, the vessel 3 was composed of graphite, which is a dielectric material. The vessel had a diameter of 18 mm and a height of 37 mm. The through-hole material used was glass beads having a diameter of 2 mm. Into the vessel 3, 2.04 g of a coal sample, which had been crushed to a particle size of 2 mm or less and then dried in vacuum at room temperature, was charged. A weight having a weight of 200 g was fallen a fall length of 20 mm 5 times on the coal sample to pack the sample 1 (the thickness of the sample layer reached 10 mm in this state). Subsequently, the glass beads having a diameter of 2 mm were arranged on the layer packed with the sample 1 at a thickness of 25 mm. A sillimanite disc having a diameter of 17 mm and a thickness of 5 mm was disposed on the glass-bead packed layer. A swelling coefficient detection rod 13, which was a quartz rod, was disposed on the disc. A weight 14 weighing 1.3 kg was disposed on the upper portion of the quartz rod. Thus, the pressure that acted on the sillimanite disc was 50 kPa. The inert gas used was nitrogen gas, and heating was performed to 550° C. at a heating rate of 3° C./min. After completion of heating, cooling was performed in a nitrogen atmosphere. In the cooled vessel, the mass of the plastic coal and the mass of the beads that did not adhere to one another were measured. The above-described measurement conditions are determined as preferred conditions for measuring permeation distance by the inventors of the present invention on the basis of a comparison of measurement results obtained under various conditions. However, the method for measuring permeation distance is not limited to the above-described method.

The glass-bead layer is formed so as to have a thickness larger than or equal to the permeation distance. If plastic coal permeates through the glass-bead layer until the plastic coal reaches the uppermost portion of the glass-bead layer during measurement, the amount of the glass beads is increased and remeasurement is conducted. The inventors of the present invention conducted an examination in which the thickness of the glass-bead layer was changed to various values and confirmed that all the permeation distances measured using the same sample became equal as long as the thickness of the glass-bead layer was larger than or equal to the permeation distance. When a caking additive having a large permeation distance was measured, a larger vessel was used and the amount of glass beads packed was increased to conduct the measurement.

It was also confirmed that, even when a permeation distance was determined by a method similar to that described above using, as the heating element 8, an electric furnace that employs resistance heating and a sample vessel made of glass, permeation distances measured using the same brand became substantially equal to the permeation distance measured by the method used in Example 1.

TABLE 1

| Coal | Ro [%] | log MF [log ddpm] | VM [mass %] | Ash [mass %] | Permeation distance [mm] |
|---|---|---|---|---|---|
| Coal A | 0.66 | 3.55 | 43.2 | 5.8 | 8.0 |
| Coal B | 0.67 | 1.00 | 36.6 | 9.0 | 3.3 |
| Coal C | 0.72 | 3.61 | 40.8 | 9.0 | 14.9 |
| Coal D | 0.73 | 2.29 | 36.2 | 8.8 | 8.1 |
| Coal E | 0.75 | 2.32 | 38.1 | 9.7 | 8.0 |
| Coal F | 0.80 | 3.17 | 37.2 | 7.9 | 19.5 |
| Coal G | 0.91 | 3.59 | 33.0 | 7.9 | 19.0 |
| Coal H | 1.02 | 2.48 | 29.1 | 8.6 | 6.3 |
| Coal I | 1.00 | 1.71 | 25.8 | 9.6 | 2.5 |
| Coal J | 1.00 | 2.20 | 27.7 | 10.4 | 4.8 |
| Coal K | 1.03 | 2.97 | 28.2 | 9.6 | 12.1 |
| Coal L | 1.14 | 1.77 | 24.2 | 9.2 | 4.9 |
| Coal M | 1.30 | 1.34 | 21.0 | 9.4 | 1.3 |
| Coal N | 1.31 | 1.26 | 20.4 | 7.3 | 0.9 |
| Coal O | 1.38 | 2.49 | 20.9 | 10.9 | 8.7 |
| Coal P | 1.44 | 2.03 | 21.1 | 9.3 | 7.8 |
| Coal Q | 1.54 | 0.00 | 16.6 | 8.3 | 1.2 |
| Coal R | 1.62 | 0.70 | 18.8 | 9.6 | 3.0 |
| Caking additive S | — | 4.8 or more | — | Less than 1 | 65.0 |

The height of a layer in which beads adhere to one another was considered to be a permeation distance. The relationship between the height and the mass of glass-bead-packed layer was determined in order to derive the height of the packed glass beads from the mass of the beads to which the plastic coal adhered. As a result, Expression (5) was obtained and used to derive a permeation distance.

$$L = (G - M) \times H \quad (5)$$

Where L represents a permeation distance [mm], G represents the mass [g] of the packed glass beads, M represents the mass [g] of beads that do not adhere to plastic coal, and H represents the height [mm/g] of the packed layer per gram of glass beads packed in the testing apparatus.

Figure 9:
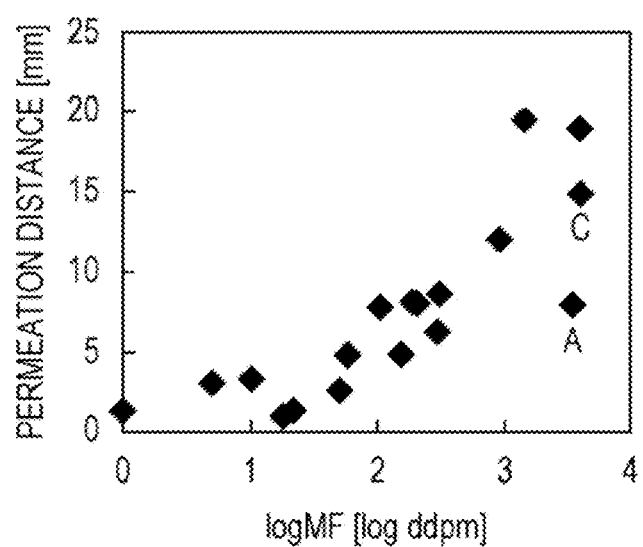
FIG. 9 is a graph showing the results of measuring the permeation distance of plastic coal in the present invention.

FIG. 9 shows the relationship between the results of measuring permeation distances and the logarithm (log MF) of Gieseler maximum fluidity (MF). According to FIG. 9, the permeation distances measured in Example 1 showed a correlation with the values of maximum fluidity. However, even when the values of MF are substantially equal, the values of permeation distance differ from each other. Considering that, for example, the results of studies on the error in measuring a permeation distance using the apparatus showed that the standard deviation obtained from the results of testing performed 3 times under the same conditions was 0.6, a significant difference in permeation distance existed between Coal A and Coal C, whose values of maximum fluidity were substantially equal to each other.

In order to examine the relationship between the size of the particles of coal having a permeation distance larger than or equal to the above-described critical permeation distance and coke strength, a coal blend including 20% by mass of Coal A having a permeation distance less than the critical permeation distance and a coal blend including 20% by mass of Coal F having a permeation distance larger than or equal to the critical permeation distance were prepared as described below, and the strength of coke made by carbonization was measured for each case where the size of the particles of Coal A or Coal F was changed to a specific value.

In an existing coal-blending theory for estimating coke strength, it has been considered that coke strength is defined mainly by the mean maximum reflectance of vitrinite (Ro) and the value of log MF of coal (e.g., see Non Patent Literature 1). Accordingly, coal blends including various coals were prepared so that all the weighted averages Ro of all the coal blends were equal and all the weighted averages log MF of all the coal blends were equal (Ro=0.99, log MF=2.2). Coal A and Coal F were crushed until the proportion of the particles thereof having a diameter less than 1 mm, 3 mm, or 6 mm reached 100% by mass. Other coals were crushed until the proportion of the particles thereof having a diameter less than 3 mm reached 100% by mass. Using these coals, 6 standards of coal blends shown in Table 2 were prepared. In Table 2, "%" used for Coal A to Coal R included in each coal blend always denotes "% by mass".

TABLE 2

| Coal | Blending proportions | | | | | |
|---|---|---|---|---|---|---|
| | Coal blend A1 [%] | Coal blend A2 [%] | Coal blend A3 [%] | Coal blend F1 [%] | Coal blend F2 [%] | Coal blend F3 [%] |
| Coal A | 20 | 20 | 20 | 0 | 0 | 0 |
| Coal B | 14 | 14 | 14 | 13 | 13 | 13 |
| Coal F | 0 | 0 | 0 | 20 | 20 | 20 |
| Coal H | 19 | 19 | 19 | 20 | 20 | 20 |
| Coal J | 13 | 13 | 13 | 20 | 20 | 20 |
| Coal L | 11 | 11 | 11 | 11 | 11 | 11 |
| Coal N | 11 | 11 | 11 | 7 | 7 | 7 |
| Coal O | 8 | 8 | 8 | 9 | 9 | 9 |
| Coal R | 4 | 4 | 4 | 0 | 0 | 0 |
| Maximum particle diameters [mm] of Coal A and Coal F | 1 | 3 | 6 | 1 | 3 | 6 |
| Weighted average Ro [%] | 0.99 | 0.99 | 0.99 | 0.99 | 0.99 | 0.99 |
| Weighted average log MF [log ddpm] | 2.2 | 2.2 | 2.2 | 2.2 | 2.2 | 2.2 |
| DI 150/15 [—] | 80.0 | 78.8 | 78.5 | 79.6 | 76.9 | 74.3 |
| CSR [%] | 58.0 | 55.9 | 55.2 | 57.6 | 50.5 | 47.5 |
| MSI + 65 [%] | 53.0 | 51.8 | 51.5 | 52.4 | 49.5 | 46.7 |

The permeation distance of Coal A was 8.0 mm, which was less than the critical permeation distance defined by the criterion described in (III). The permeation distance of Coal F was 19.5 mm, which was larger than the critical permeation distance defined by the criterion described in (III).

Figure 10:
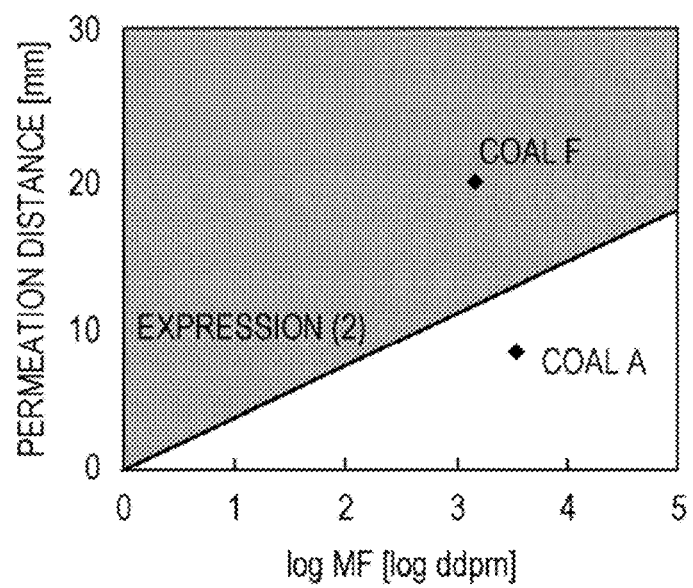
FIG. 10 is a graph showing the positional relationship between the permeation distances and the values of maximum fluidity of Coal A and Coal F used in Example 1 and the critical permeation distance calculated by the method described in (I).
Figure 11:
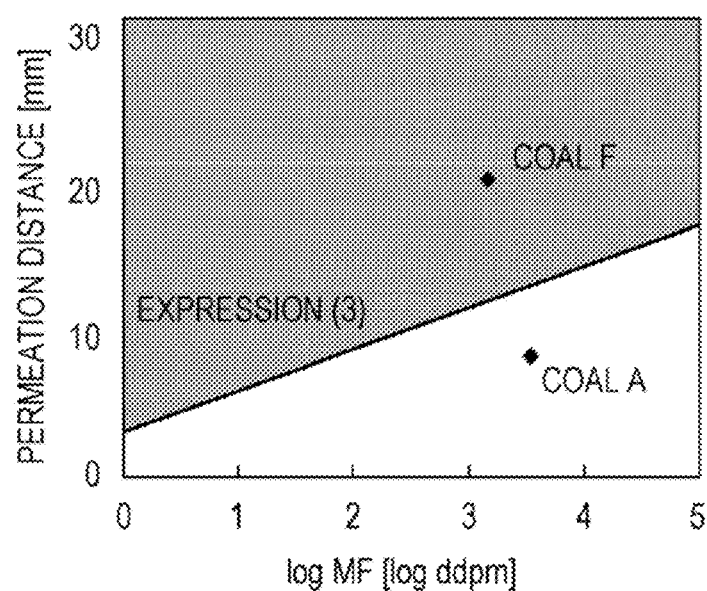
FIG. 11 is a graph showing the positional relationship between the permeation distances and the values of maximum fluidity of Coal A and Coal F used in Example 1 and the critical permeation distance calculated by the method described in (II).

The constants a and a' used in Expressions (2) and (3), respectively, were set to 2.70, which corresponded to the slope of a regression line obtained from the permeation distances and the values of maximum fluidity of coals that constituted the coal blend and fell within the range of log MF<2.5. The constant b of Expression (3) was set to 3.0 on the basis of a value 5 times 0.6 of the standard deviation obtained under measurement conditions of the invention examples. FIGS. 10 and 11 show the results of examining the positional relationships of the permeation distance and maximum fluidity of the coal used in Example 1 and the critical permeation distance described in (I) and (II) above using Expressions (2) and (3), respectively. FIGS. 10 and 11 show that Coal F was coal having a permeation distance larger than or equal to the critical permeation distances described in (I) and (II) and Coal A was coal having a permeation distance less than the critical permeation distances described in (1) and (II).

The moisture content in the entirety of each coal blend described in Table 2 was controlled to be 8% by mass, and a carbonization can was packed with 16 kg of the resulting coal blend at a packing density of 750 kg/m. While a weight of 10 kg was disposed on the coal blend, carbonization was performed for 6 hours in an electric furnace having a furnace-wall temperature of 1050° C. The resulting product was taken from the furnace and subjected to a nitrogen cooling. Thus, cokes were prepared. The strength of each coke was calculated as a drum index DI150/15, which is the ratio of the proportion of the mass of the coke particles having a diameter of 15 mm or more which is measured after performing 150 rotations at 15 rpm to the proportion measured before the rotation in accordance with a rotation strength testing method according to JIS K 2151. The results of measuring CSR (coke strength after a $CO_2$ reaction, measured in accordance with the ISO 18894) and micro strength index (MSI+65) are also shown.

Figure 12:
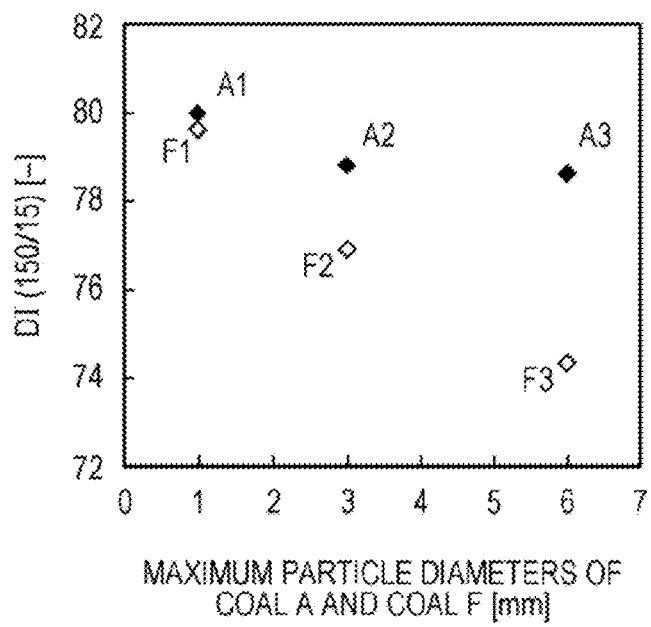
FIG. 12 is a graph showing the results of measuring the drum index of coke in Example 1.

The results of measuring drum index are also shown in Table 2. FIG. 12 shows the relationships between the maximum particle diameter of Coal A and Coal F and the drum index. It was confirmed that, regardless of the particle size, the coal blend including Coal F having a permeation distance larger than or equal to the above-described critical permeation distance had a lower strength than the coal blend including Coal A having a permeation distance less than the critical permeation distance. There was a difference in coke strength although the values of log MF of Coal A and Coal F did not greatly differ and the tests were conducted under conditions where all the values of weighed average log MF of all the coal blends were set equal. Thus, it was confirmed that the value of permeation distance measured in the present invention was a factor that affects strength and that cannot be interpreted using existing factors. It was also confirmed that coke strength can be increased by reducing the size of coal particles in both cases where the coal blend including Coal A having a permeation distance less than the above-described critical permeation distance was used and where the coal blend including Coal F having a permeation distance larger than or equal to the critical permeation distance was used. In particular, a significant increase of strength due to the reduction in the size of coal particles was observed in the case where the coal blend including Coal F having a permeation distance larger than or equal to the critical permeation distance was used.

Example 2

Determination of the Particle Size Preferable for Charging Coal Having a Permeation Distance Larger than or Equal to the Critical Permeation Distance into a Coke Oven The degree to which the size of the particles of coal having a permeation distance larger than or equal to the critical permeation distance is to be reduced was studied using an actual coke oven. Generally, in a standard operation of an actual coke oven, in many cases, coals are crushed after individual brands of coals are mixed together in a predetermined blending proportions. At this time, the size of the particles of a coal blend is managed using the ratio of the mass of particles that remain on or that pass through a sieve when the coal blend is passed through the sieve having a particular standard to the total mass. Therefore, in many cases, it is difficult to control the size of the particles for each brand constituting the coal blend.

The inventors of the present invention conducted carbonization of coal blends each prepared by changing the blending proportions of coal or a caking additive having a permeation distance larger than or equal to the critical permeation distance in an actual coke oven. Then, the inventors measured a drum index DI150/15 as the strength of coke made by carbonization and studied the relationship between the proportion of particles having a diameter of 6 mm or more in a coal blend and coke strength. On the basis of the results, the inventors studied the degree to which coal having a permeation distance larger than or equal to the critical permeation distance is to be crushed.

Table 3 shows the average properties of the coal blends used, carbonization temperature, and temperature at the center of carbonization chamber measured after carbonization. The fluctuation ranges of the average properties of the coal blends used, carbonization temperature, and temperature at the center of carbonization chamber measured after carbonization were set small in order to eliminate the impact of these factors on coke strength as possible.

TABLE 3

| Average properties of coal blends | Ro [%] | 0.98 to 1.02 |
|---|---|---|
| | log MF [log ddpm] | 2.6 to 2.8 |
| | Moisture content [%] | 8.5 to 10.5 |
| Carbonization conditions | Carbonization temperature [° C.] | 1090 to 1105 |
| | Temperature measured at the center of carbonization chamber after carbonization [° C.] | 990 to 1115 |

FIG. 13 shows the relationship between the proportion of particles having a diameter of 6 mm or more in a coal blend and the measured coke strength. As shown in FIG. 13, it was confirmed that, in the case where the blending proportion of coal having a permeation distance larger than or equal to the critical permeation distance was relatively large, that is, 8% by mass or more and less than 12% by mass, when the size of the particles of the entire coal was increased due to an increase in the proportion of particles having a diameter of 6 mm or more in the coal, a reduction in coke strength occurred. In contrast, when a coal blend in which the content of coal having a permeation distance larger than or equal to the critical permeation distance was 2% by mass or less, a reduction in strength due to the increase in the size of the particles of coal was small. This proves that, even when coal blends have the same particle size as a whole, a coal blend including coal having a permeation distance larger than or equal to the critical permeation distance experiences a reduction in coke strength. It is shown that, when the proportion of particles having a size of 6 mm or more in the coal blend is about 5% by mass or less, the coke strength becomes substantially equal regardless of whether the coal blend includes the coal having a permeation distance larger than or equal to the critical permeation distance. It is difficult to measure the size of the particles of only coal having a permeation distance larger than or equal to the critical permeation distance which is mixed in a coal blend that has been crushed. However, according to the test results, it is assumed that a reduction in coke strength caused due to mixing of coal having a permeation distance larger than or equal to the critical permeation distance can be suppressed by crushing the coal having a permeation distance larger than or equal to the critical permeation distance until the content of particles having a size of 6 mm or more reaches 5% by mass or less. This is presumably because, since coal having a large permeation distance is likely to form oversized voids as shown in FIG. 5, formation of oversized voids is suppressed by reducing the content of coal particles having a large diameter and this contributes to an increase in coke strength.

Example 3

Determination of Conditions for an Individual Brand in Order to Pulverize Coal Having a Permeation Distance Larger than or Equal to the Critical Permeation Distance in a Coke Plant Until the Content of Particles Having a Size of 6 mm or More Reaches 5% by Mass Under the same crushing conditions, the larger the size of the particles of coal supplied to a crusher and the harder the coal, the larger the size of the crushed particles of the coal. Thus, the conditions for the size of the particles of coal to be supplied in order to crush coal having a permeation distance larger than or equal to the critical permeation distance in a normal coke plant until the content of particles having a size of 6 mm or more reaches 5% by mass, were studied. As a result, it was found that, when the size of the particles of an individual brand of coal having a permeation distance larger than or equal to an average critical permeation distance which has not yet been crushed in a coke plant is such that the content of particles having a size of 6 mm or more in the coal is 30% by mass or less, the coal can be crushed in the coke plant until the content of particles having a size of 6 mm or more reaches 5% by mass.

Considering the hardness of coal (grindability), when the size of the particles of coal that has not yet been crushed is such that:

$$\text{Content (\%) of particles having a diameter of 6 mm or more} \leq 30 + 0.5 \times (HGI - 60) \quad (1),$$

the coal can be crushed in the coke plant until the content of particles having a size of 6 mm or more reaches 5% by mass. Where HGI is an index determined by a grindability testing method described in JIS M 8801.

Example 4

Effect of Controlling the Size of the Particles of an Individual Brand on Increasing Coke Strength In coal that is normally mined and subjected to a coal cleaning treatment in a production field of Coal G and then shipped from the production field, the content of particles having a diameter of 6 mm or more is 39% by mass. Coal G that had been subjected to a coal cleaning was crushed using an impact crusher to prepare coal in which the content of particles having a size of 6 mm or more in the coal was 30% by mass (hereinafter, this coal is referred to as Coal G'). After Coal G and Coal G' arrived at a coke plant, Coal G and Coal G' were each mixed with Coals A, B, H, J, L, N, O, and R with blending proportions of Coal G and Coal G' being set to 10% by mass to prepare a coal blend having a weighted average reflectance of 1.01% and a weighted average log MF of 2.4. The permeation distances of Coal G and Coal G' were 19.0 mm as measured by the method described in Example 1. Thus, Coal G and Coal G' were coals having a permeation distance larger than or equal to the critical permeation distance with reference to any criterion defined in (I) to (III).

Coal blend g including Coal G and Coal blend g' including Coal G' were each crushed using an impact crusher installed in the coke plant until the content of particles having a size of 3 mm or less reached 78% by mass. In Coal blend q and Coal blend g' that had been crushed, the content of particles having a size of 6 mm or more was 5.5% by mass. The coal blends were subjected to carbonization in a coke oven at an operating ratio of 125%. The resulting cokes were dry-quenched. Subsequently, measurement of JIS drum index DI150/15 was performed. While the strength index of a coke made from Coal blend g was 82.9, the strength index of a coke made from Coal blend g' was 83.1. Thus, it was confirmed that coke strength can be increased by controlling an individual brand of coal prior to arrival at a coke plant so that the content of particles having a size of 6 mm or more in the coal reaches 30% by mass.

Comparative Example 1

A test similar to the above-described test was conducted using Coal K (when normally shipped from its production field, the content of particles having a size of 6 mm or more was 37% by mass) instead of Coal G. Coke strength was 83.0 in both cases where the content of particles having a size of 6 mm or more in Coal K was reduced and was not reduced to 30% by mass. Thus, the effect on increasing coke strength was not confirmed. Coal K is coal having a permeation distance less than the critical permeation distance in accordance with any criterion defined in (I) to (III). Thus, the effect of applying the method according to the present invention to coal having a permeation distance larger than or equal to the critical permeation distance was confirmed.

REFERENCE SIGNS LIST 1 sample
2 through-hole material having through holes from top to bottom surfaces
3 vessel
5 sleeve
7 thermometer
8 heating element
9 temperature sensor
10 temperature controller
11 gas introduction port
12 gas exhaust port
13 swelling coefficient detection rod
14 weight
15 displacement gage
16 circular through-holes
17 packing particles
18 circular packed cylinders
19 coal or caking additive having a permeation distance of the critical permeation distance or more
20 coal or caking additive having a permeation distance of less than the critical permeation distance
21 pores
22 oversized voids

The invention claimed is:

1. A method for preparing coal for coke making, in which an individual brand of coal or caking additive is prepared at a time prior to arrival at a coke plant, the individual brand of coal or caking additive being used alone or in mixture with another coal as a raw material for coke making,
wherein, when the individual brand of coal or caking additive has a permeation distance of 15 mm or more, a size of particles of the individual brand of coal or caking additive is controlled at the time prior to arrival at the coke plant so that a content of particles having a diameter of 6 mm or more in the individual brand of coal or caking additive reaches 30% by mass or less, the permeation distance being measured by a method including the following steps (A) to (D):
(A) crushing the individual brand of coal or caking additive until a content of particles having a diameter of 2 mm or less reaches 100% by mass and then packing a vessel with the individual brand of coal or caking additive that has been crushed at a bulk density of 0.8 g/cm$^3$ and at a thickness of 10 mm to prepare a sample;
(B) arranging glass beads having a diameter of 2 mm on the sample at a thickness of the permeation distance or more;
(C) while applying a load of 50 kPa to an upper portion of the glass beads, performing heating in an inert gas atmosphere from room temperature to 550° C. at a heating rate of 3° C./min; and
(D) measuring a permeation distance of the softened sample that has permeated a layer composed of the glass beads.

2. A method for preparing coal for coke making, in which an individual brand of coal or caking additive is prepared at a time prior to arrival at a coke plant, the individual brand of coal or caking additive being used alone or in mixture with another coal as a raw material for coke making,
wherein, when the individual brand of coal or caking additive has a permeation distance of 15 mm or more, a size of particles of the individual brand of coal or caking additive is controlled at the time prior to arrival at the coke plant,
so that a content of particles having a diameter of 6 mm or more in the individual brand of coal or caking additive, the content being determined from a Hardgrove grindability index HGI of the individual brand of coal or caking additive using Expression (1) below, is achieved:

$$\text{Content (mass \%) of particles having a diameter of } 6 \text{ mm or more} \leq 30 + 0.5 \times (\text{HGI} - 60) \quad (1),$$

the permeation distance being measured by a method including the following steps (A) to (D):
(A) crushing the individual brand of coal or caking additive until a content of particles having a diameter of 2 mm or less reaches 100% by mass and then packing a vessel with the individual brand of coal or caking additive that has been crushed at a bulk density of 0.8 g/cm$^3$ and at a thickness of 10 mm to prepare a sample;

(B) arranging glass beads having a diameter of 2 mm on the sample at a thickness of the permeation distance or more;

(C) while applying a load of 50 kPa to an upper portion of the glass beads, performing heating in an inert gas atmosphere from room temperature to 550° C. at a heating rate of 3° C./min; and (D) measuring a permeation distance of the softened sample that has permeated a layer composed of the glass beads.

3. A method for preparing coal for coke making, in which an individual brand of coal or caking additive is prepared at a time prior to arrival at a coke plant, the individual brand of coal or caking additive being used alone or in mixture with another coal as a raw material for coke making, wherein, on the basis of a relationship between a critical permeation distance and a Gieseler maximum fluidity, the relationship being obtained from permeation distances and values of Gieseler maximum fluidity of one or more brands of coal or caking additive, when a permeation distance of the individual brand of coal or caking additive is larger than or equal to a critical permeation distance calculated from a Gieseler maximum fluidity of the individual brand of coal or caking additive on the basis of the relationship between the critical permeation distance and the Gieseler maximum fluidity, a size of particles of the individual brand of coal or caking additive is controlled at the time prior to arrival at the coke plant so that a content of particles having a diameter of 6 mm or more in the individual brand of coal or caking additive reaches 30% by mass or less.

4. A method for preparing coal for coke making, in which an individual brand of coal or caking additive is prepared at a time prior to arrival at a coke plant, the individual brand of coal or caking additive being used alone or in mixture with another coal as a raw material for coke making, wherein, on the basis of a relationship between a critical permeation distance and a Gieseler maximum fluidity, the relationship being obtained from permeation distances and values of Gieseler maximum fluidity of one or more brands of coal or caking additive, when a permeation distance of the individual brand of coal or caking additive is larger than or equal to a critical permeation distance calculated from a Gieseler maximum fluidity of the individual brand of coal or caking additive on the basis of the relationship between the critical permeation distance and the Gieseler maximum fluidity, a size of particles of the individual brand of coal or caking additive is controlled at the time prior to arrival at the coke plant, so that a content of particles having a diameter of 6 mm or more in the individual brand of coal or caking additive, the content being determined from a Hardgrove grindability index HGI of the individual brand of coal or caking additive using Expression (1) below, is achieved:

Content (mass %) of particles having a diameter of 6 mm or more≤30+0.5×(HGI−60)    (1).

5. The method for preparing coal for coke making according to claim 3, wherein the critical permeation distance is calculated using Expression (2) below:

Critical permeation distance=1.3×$a$×log MF$c$    (2)

where "a" represents a constant 0.7 to 1.0 times a coefficient of log MF in a regression line crossing an origin point, the regression line being obtained using permeation distances and values of log MF of one or more coals that fall within a range of common logarithm of Gieseler maximum fluidity log MF<2.5, and MFc represents a Gieseler maximum fluidity (ddpm) of the coal or caking additive to be prepared.

6. The method for preparing coal for coke making according to claim 4, wherein the critical permeation distance is calculated using Expression (2) below:

Critical permeation distance=1.3×$a$×log MF$c$    (2)

where "a" represents a constant 0.7 to 1.0 times a coefficient of log MF in a regression line crossing an origin point, the regression line being obtained using permeation distances and values of log MF of one or more coals that fall within a range of common logarithm of Gieseler maximum fluidity log MF<2.5, and MFc represents a Gieseler maximum fluidity (ddpm) of the coal or caking additive to be prepared.

7. The method for preparing coal for coke making according to claim 5, wherein a represents a constant 0.7 to 1.0 times a coefficient of log MF in a regression line crossing an origin point, the regression line being obtained using permeation distances and values of common logarithm of Gieseler maximum fluidity log MF of one or more coals that fall within a range of 1.75<log MF<2.50.

8. The method for preparing coal for coke making according to claim 6, wherein a represents a constant 0.7 to 1.0 times a coefficient of log MF in a regression line crossing an origin point, the regression line being obtained using permeation distances and values of common logarithm of Gieseler maximum fluidity log MF of one or more coals that fall within a range of 1.75<log MF<2.50.

9. The method for preparing coal for coke making according to claim 3, wherein the critical permeation distance is calculated using Expression (3) below:

Permeation distance=$a'$×log MF$c$+$b$    (3)

where "a" represents a constant 0.7 to 1.0 times a coefficient of log MF in a regression line crossing an origin point, the regression line being obtained using permeation distances and values of log MF of one or more coals that fall within a range of common logarithm of Gieseler maximum fluidity log MF<2.5, "b" represents a constant that is larger than or equal to and five times or less an average of standard deviations each obtained by measuring, a plurality of times, the corresponding one of samples taken from one or more brands used for preparing the regression line, and MFc represents a Gieseler maximum fluidity (ddpm) of the coal or caking additive to be prepared.

10. The method for preparing coal for coke making according to claim 4, wherein the critical permeation distance is calculated using Expression (3) below:

Permeation distance=$a'$×log MF$c$+$b$    (3)

where "a" represents a constant 0.7 to 1.0 times a coefficient of log MF in a regression line crossing an origin point, the regression line being obtained using permeation distances and values of log MF of one or more coals that fall within a range of common logarithm of Gieseler maximum fluidity log MF<2.5, "b" represents a constant that is larger than or equal to and five times or less an average of standard deviations each obtained by measuring, a plurality of times, the corresponding one of samples taken from one or more brands used for preparing the regression line, and MFc represents a Gieseler maximum fluidity (ddpm) of the coal or caking additive to be prepared.

11. The method for preparing coal for coke making according to claim 9, wherein "a" represents a constant 0.7 to 1.0 times a coefficient of log MF in a regression line crossing an origin point, the regression line being obtained using permeation distances and values of common logarithm of Gieseler maximum fluidity log MF of one or more coals that fall within a range of 1.75<log MF<2.50.

12. The method for preparing coal for coke making according to claim 10, wherein "a" represents a constant 0.7 to 1.0 times a coefficient of log MF in a regression line crossing an origin point, the regression line being obtained using permeation distances and values of common logarithm of Gieseler maximum fluidity log MF of one or more coals that fall within a range of 1.75<log MF<2.50.

13. The method for preparing coal for coke making according to claim 1, wherein the time prior to arrival at a coke plant is a time prior to shipping from a coal field or a caking-additive manufacturing field.

14. The method for preparing coal for coke making according to claim 2, wherein the time prior to arrival at a coke plant is a time prior to shipping from a coal field or a caking-additive manufacturing field.

15. The method for preparing coal for coke making according to claim 3, wherein the time prior to arrival at a coke plant is a time prior to shipping from a coal field or a caking-additive manufacturing field.

16. The method for preparing coal for coke making according to claim 4, wherein the time prior to arrival at a coke plant is a time prior to shipping from a coal field or a caking-additive manufacturing field.

* * * * *